United States Patent
Koning et al.

(10) Patent No.: US 10,066,053 B2
(45) Date of Patent: Sep. 4, 2018

(54) ALKYD RESIN COMPOSITIONS

(71) Applicant: DSM IP Assets B.V., Heerlen (NL)

(72) Inventors: Cornelis Eme Koning, Echt (NL);
Paulus Franciscus Anna Buijsen, Echt (NL); Adrianus Jozephus Hendricus Lansbergen, Echt (NL); Alwin Papegaaij, Echt (NL); Douglas Hayden, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/535,549

(22) PCT Filed: Dec. 21, 2015

(86) PCT No.: PCT/EP2015/080749
§ 371 (c)(1),
(2) Date: Jun. 13, 2017

(87) PCT Pub. No.: WO2016/097404
PCT Pub. Date: Jun. 23, 2016

(65) Prior Publication Data
US 2017/0327636 A1      Nov. 16, 2017

(30) Foreign Application Priority Data
Dec. 19, 2014 (EP) .................................. 14199363

(51) Int. Cl.
*C08G 63/685* (2006.01)
*C09D 167/08* (2006.01)

(52) U.S. Cl.
CPC ......... *C08G 63/685* (2013.01); *C09D 167/08* (2013.01)

(58) Field of Classification Search
CPC ............................ C08G 63/685; C09D 167/08
See application file for complete search history.

(56) References Cited

U.S. PATENT DOCUMENTS 3,960,799 A      6/1976   Mosimann et al.

FOREIGN PATENT DOCUMENTS

| JP | 1-207362 | 8/1989 |
| JP | 01207362 A * | 8/1989 |

(Continued)

OTHER PUBLICATIONS

International Search Report for PCT/EP2015/080749, dated Feb. 22, 2016, 4 pages.

(Continued)

*Primary Examiner* — Vu A Nguyen
(74) *Attorney, Agent, or Firm* — Nixon & Vanderhye P.C.

(57) ABSTRACT

The present invention relates to an alkyd resin composition comprising a. 1-60 wt % of an imide compound according to anyone of formulas Ia, Ib, Ic, Id or Ie wherein R1 is H or a C1-C20 optionally substituted hydrocarbon group; R2 and R5 are independently H, or a C1-C20 hydrocarbon group; R3 and R4 are independently H, or a C1-C20 hydrocarbon group; R6 is H or a methyl group; R7 and R8 are independently H, methyl or ethyl; b. 10-40 wt % of an alcohol having a number average hydroxy functionality ≥2.0; c. 30-70 wt % of fatty acids or vegetable oils; d. 0-50 wt % of a mono and/or polyfunctional compound capable of esterification, which compound is different from the compounds used in a, b and c; wherein the wt % is determined relative to the total of weight of compounds a, b, c and d.

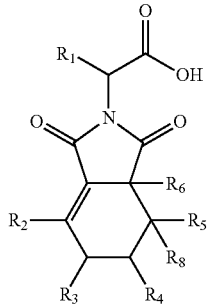

Ia

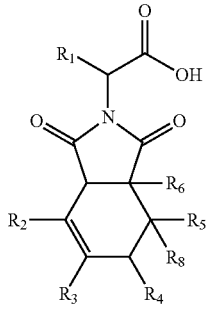

Ib

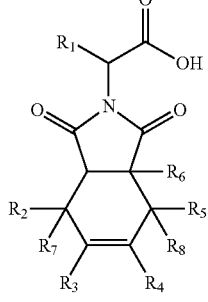

Ic

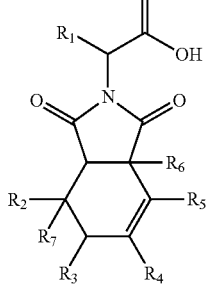

Id (Continued)

-continued

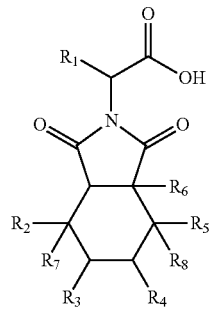

Ie

14 Claims, No Drawings

(56) References Cited

FOREIGN PATENT DOCUMENTS

WO  WO 2008/101722   8/2008
WO  WO 2014/044732   3/2014

OTHER PUBLICATIONS

Written Opinion of the ISA for PCT/EP2015/080749, dated Feb. 22, 2016, 6 pages.
International Preliminary Report on Patentability for PCT/EP2015/080749, dated Mar. 13, 2017, 52 pages.

* cited by examiner

ALKYD RESIN COMPOSITIONS

This application is the U.S. national phase of International Application No. PCT/EP2015/080749 filed 21 Dec. 2015, which designated the U.S. and claims priority to EP Patent Application No. 14199363.4 filed 19 Dec. 2014, the entire contents of each of which are hereby incorporated by reference.

The present invention relates to alkyd resin compositions comprising specific imides, alkyd resins prepared from said imides, coatings prepared from said alkyd resins and articles coated with said coatings.

Alkyd resins are known in the art. Many publications exist that describe the resin compositions and the compounds used to prepare the resin compositions.

WO2008/101722 describes grafted autooxidisable polyester resins, wherein the resin is prepared by grafting of at least a diacid or its anhydride onto a first agent by a Diels-Alder and/or Ene reaction, followed by a reaction with a second agent. A disadvantage of the resin composition of WO2008/101722 is the slow drying, and sometimes yellowing of the product.

In general, paints (such as alkyd paints) for professional and do-it-yourself applications are subject to increasing technical and ecological restrictions. Emissions of volatile organic compounds (VOC) must be reduced to protect the environment. Polyester resins with a high content of solids and/or which are water borne (such as alkyd resins) have been used to address the problem of VOC. Nowadays, it is also desirable that paints are obtained from sustainable sources. It is therefore a preferred object of the invention that the resins have a high biorenewable content as defined herein.

The invention relates to an alkyd resin composition comprising
  a. 1-60 wt % of an imide compound according to anyone of formulas Ia, Ib, Ic, Id or Ie,

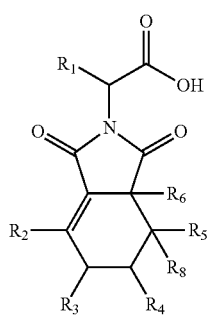

Ia

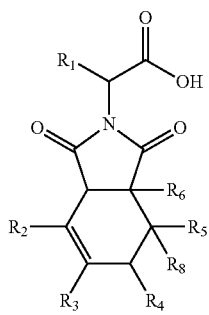

Ib

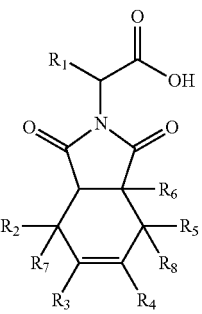

Ic

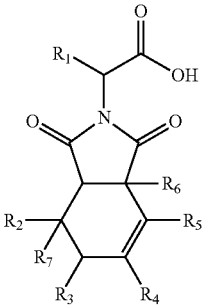

Id

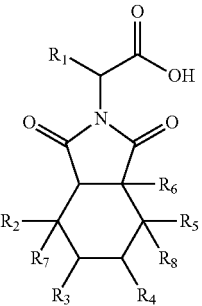

Ie wherein R1 is H or a C1-C20 optionally substituted hydrocarbon group;
R2 and R5 are independently H, or a C1-C20 hydrocarbon group;
R3 and R4 are independently H, or a C1-C20 hydrocarbon group;
R6 is H or a methyl group;
R7 and R8 are independently H, methyl or ethyl;
  b. 10-40 wt % of an alcohol having a number average hydroxy functionality ≥2.0;
  c. 30-70 wt % of fatty acids or vegetable oils;
  d. 0-50 wt % of a mono and/or polyfunctional compound capable of esterification (such as for example those containing OH and/or COOH groups), which compound is different from the compounds used in a, b and c,
wherein the wt % is determined relative to the total of weight of compounds a, b, c and d.

In addition to the environmental friendly and sustainable nature of the compounds Ia-Ie used in the present invention, the alkyd resin compositions may result in coatings having similar or even improved properties, like hardness, yellowing and gloss retention, compared to when using similar alkyd resin compositions in which at least part of the compounds Ia-Ie are replaced with benzoic acid.

The compounds according to formulas Ia-d are maleimide based Diels Alder adducts (R6=H), or preferably citraconimide based Diels Alder adducts (R6=methyl). The compound according to formula Ie is the hydrogenated Diels Alder adduct of the compound as defined in anyone of formulas Ia-Id.

An imide group is a functional group consisting of two acyl groups bound to nitrogen.

The compounds according to formulas Ia-Id can be up to 100% biobased in case the imide is formed by reacting maleic acid or citraconic acid, or their anhydrides maleic anhydride or citraconic anhydride, with an aminoacid to yield maleimide or citraconimide compounds, which can be reacted with a conjugated diene to render the compounds according to formula Ia-d, and optionally hydrogenated to the compound according to formula Ie.

In a preferred embodiment R6 is a methyl group, such that the compounds are citraconimide based Diels-Alder adducts.

R1 can be H or a C1-C20 optionally substituted hydrocarbon group. Preferably the N—C(R1)-COOH fragment stems from an aminoacid which has been reacted with maleic acid, citraconic acid, or their anhydrides. Examples of R1 are H, methyl, hydroxymethyl, 1-hydroxyethyl, isopropyl, sec-butyl, 2-methyl-propyl, 2(methylthio)ethyl, benzyl, tolyl, parahydroxytolyl, or any other organic fragment from aminoacids such as for example arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine and tryptophan. More preferably R1 is H or a C1-C20 hydrocarbon group, Preferred examples of C1-C20 hydrocarbon groups are methyl, isopropyl, sec-butyl, 2-methyl-propyl, benzyl and tolyl. Most preferred examples are H and benzyl.

R2, R3, R4 and R5 are independently H, or a C1-C20 hydrocarbon group. R2 and R5, R3 and R4 or R2 and R4 can form a fused ring, for example a cyclic structure like a 5-membered or 6-membered ring structure. Preferably, R2 and R5 are independently selected from the group consisting of H, methyl and ethyl. More preferably, R2 and R5 are independently H or methyl. Even more preferably R2 and R5 are methyl. Preferably R3 and R4 are H.

The compounds Ia, Ib, Ic, and Id are isomers: the main difference between the compounds is the position of the double bond which resides after completion of the Diels Alder reaction of the maleimide or citraconimide with the conjugated diene. This double bond may take different positions, so that in most cases a mixture of isomeric products is obtained after reacting the maleimide or citraconimide with the conjugated diene.

R7 and R8 independently are chosen from H, methyl or ethyl. Preferably R7 and R8 are both H.

The compound according to formulas Ia-d can be prepared with a method comprising the steps of
a) Providing maleic anhydride or citraconic anhydride (formula II), or maleic acid or citraconic acid;
b) Reacting said acid or anhydride with a primary amine according to formula III to obtain a maleimide or citraconimide according to formula IV,
c) Reacting the product according to formula IV with a conjugated diene according to formula V in a Diels Alder reaction to obtain anyone of the compounds as defined in formulas Ia, Ib, Ic or Id,
wherein R1, R2, R3, R4, R5, R6, R7 and R8 are the same as defined above.

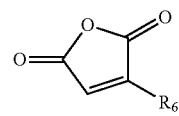

II

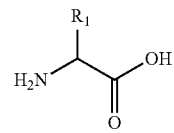

III

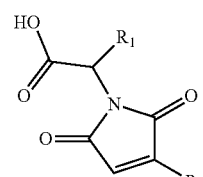

IV

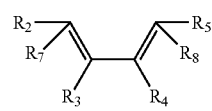

V

Alternatively the compound according to formulas Ia-d can be prepared with a method comprising the steps of
a) Providing maleic anhydride or citraconic anhydride (formula II), or maleic acid or citraconic acid;
b) Reacting said acid or anhydride with a conjugated diene according to formula V in a Diels Alder reaction to obtain an adduct;
c) Reacting the Diels Alder adduct with a primary amine according to formula III to obtain anyone of the compounds as defined in formulas Ia, Ib, Ic or Id,
wherein R1, R2, R3, R4, R5, R6, R7 and R8 are the same as defined above. Examples of dienes are butadiene, isoprene, myrcene, alpha-terpinene and alpha-phellandrene. Preferred examples of dienes are butadiene and isoprene.

Optionally it may be desirable to protect the double bond of maleic anhydride during the imidization reaction. After imidization the protection can be removed to perform the Diels Alder reaction of the maleimide.

The preparation of the adduct used in the present invention may be carried out in the conventional manner for Diels Alder additions by heating the reaction mixture, the reactants being present in substantially stoichiometric proportions or with excess of diene and optionally in a suitable organic solvent, if required for fluidity. A Diels Alder catalyst, e.g. a Lewis acid such as aluminum chloride may be employed, however un-catalyzed reactions are preferred. The reaction temperature is preferably higher than 50° C., more preferably higher than 70° C. and preferably lower than the decomposition temperature of the product. The elevated temperature is maintained for a sufficient time to obtain an acceptable yield of the adduct. The time required depends on the reactivity of the particular reagents, the temperature, the stability of the product and commercial considerations (e.g. the value of the product against the cost of prolonging the heating step), however, typically, it is greater than 30 minutes, preferably greater than one hour, more preferably greater than two hours. The preparation of the adduct used in the present invention can be effected with raised pressure as well as without raised pressure. The preparation of the adduct based on volatile reactant is preferably effected with raised pressure. The preparation of the adduct used in the present invention is preferably effected in the presence of a polymerization inhibitor, for example hydroquinone.

Prior art alkyd resins are typically obtained from a polycondensation of fatty acids or vegetable oils (30 to 70% by weight), polyols such as glycerol or pentaerythritol (10 to 40% by weight) and polyacids such as phthalic anhydride (10 to 40% by weight). These known alkyd resins have a broad molecular weight distribution and a branched structure, contain residual hydroxyl and carboxyl groups for wetting properties and are capable of autoxidative drying. Due to auto-oxidization, alkyd resins discolor in the dark and turn yellow. This tendency is even more pronounced for renewable alkyds that rosin and a high proportion of fatty acid. It is therefore desirable to find alkyd resins having improved properties.

As used herein, an alkyd resin composition is the composition of compounds used to prepare an unsaturated alkyd resin. As used herein unsaturated alkyd resin (for convenience also abbreviated herein to "alkyd resin") denotes a polyester comprising one or more unsaturated fatty acid moieties which are auto-oxidizable in air under standard conditions.

The compounds according to formulas Ia, Ib, Ic, Id or Ie may be present in the alkyd resin compositions in an amount of at least 1 wt-% and more preferably at least 5 or 10 wt-%, based on the total weight of compounds a, b, c and d. Conveniently the compounds may be present in the alkyd resin compositions in an amount of less than 60 wt-% more conveniently less than 50 wt-%.

The compounds according to formulas Ia, Ib, Ic, Id or Ie may be present in the alkyd resin compositions in an amount of from 1 to 60 wt-%, preferably from 5 to 50 wt-%, more preferably from 10 to 40 wt-%. based on the total weight of compounds a, b, c and d.

Alcohol (Compound b)

The alkyd resin composition also comprises 10-40 wt % (relative to the total weight of compounds a, b, c and d) of an alcohol having a number average hydroxy functionality ≥2.0.

Suitable alcohols may in principle be any hydroxy (i.e. OH group) functional compound or mixture of hydroxy functional compounds with a number average hydroxy functionality ≥2.0. By number average hydroxyl functionality is herein meant to take into account that even though an individual alcohol molecule has a discrete number of hydroxy groups, mixtures of alcohols typically will have a non-discrete medium hydroxy functionality. For example, one molecule may have a hydroxy functionality of 1 and another molecule may have a hydroxy functionality of 3. This will lead to a number average hydroxy functionality of 2.

In a preferred embodiment, the alcohol has a number average hydroxy functionality ≥2.5, even more preferred ≥2.8 and most preferred ≥3.

In a preferred embodiment, the alcohol has a number average hydroxy functionality of <15, preferably <10, more preferably <8, even more preferably <6, even more preferably <4.5, as this will allow for at least some of the polyol to participate in crosslinking with neighboring or the same polymer molecule.

The alcohol may comprise aliphatic parts and/or aromatic parts dependent on the required properties of the alkyd resin. The alcohol may comprise other functional groups, such as for example one or more acid groups, amine groups, urea groups, ester groups, unsaturations etc. However, it is preferred that the alcohol has only limited number of other functional groups. Particularly, it was found to be advantageous to have the amine number average functionality below about 0.2 since this reduced the yellowing considerably. It is preferred that the alcohol has only a limited number of other functional groups.

The term alcohol designates herein both individual (pure) alcohols as well as mixtures of alcohols unless otherwise stated. The individual alcohols preferably have a functionality of at least 2 to ensure that the alcohol does not act as an endcap group. The alcohol may be a mixture of several alcohols with the same or varying functionality (hydroxy and/or other functional groups).

In a preferred embodiment, at least 50 weight % of the alcohol has a hydroxy functionality ≥3, more preferably ≥4. More preferably at least 50 weight % of the alcohol has three functional groups, even more preferably at least 50 weight % of the alcohol has four functional groups. Particularly, it was found to be advantageous to utilize an alcohol, wherein at least 80 weight % of the alcohol has a hydroxy functionality ≥3, more preferably ≥4. More preferably at least 80 weight % of the alcohol has three functional groups. In a particularly preferred embodiment, the functionality of the alcohol has substantially solely hydroxy functionality, such as at least 90 weight % of the alcohol has hydroxy functionality, or the alcohol has solely (i.e. 100 weight %) hydroxy functionality.

Preferably at least 50 weight % of the alcohol is selected from the group consisting of glycerol, trimethylol propane, pentaerythritol, di-pentaerythritol, tri-pentaerythritol, isosorbide, isoidide, isomannide, hydrogenated bisphenol A, ethylene glycol, propylene glycol, poly ethylene glycol, di ethylene glycol, neo pentyl glycol, 2,3 butanediol, sugars like for example cellulose, sucrose, sorbitol, fructose and alike, polyglycerols having from 2 to 10 OH groups and mixtures thereof. In a highly preferred embodiment, the alcohol consists substantially of one or more alcohols selected from the group consisting of glycerol, trimethylol propane, pentaerythritol, isosorbide, isoidide, isomannide, hydrogenated bisphenol A, ethylene glycol, propylene glycol, polyethyleneglycol, diethylene glycol, neo pentyl glycol, 2,3 butanediol and sorbitol. By consisting substantially of is here meant that nearly all of the alcohol, such as more than 90 weight %, more than 95 weight % or more than 98 weight % of the alcohol is selected from the group consisting of glycerol, trimethylol propane, pentaerythritol, isoidide, isomannide, isosorbide, hydrogenated bisphenol A, ethylene glycol, 1.2-propylene glycol, 1.3-propylenglycol, polyethyleneglycol, diethyleneglycol, neopentylglycol, 2,3 butanediol and sorbitol. In a highly preferred embodiment, the alcohol consists of one or more alcohols selected from the group consisting of glycerol, trimethylol propane, pentaerythritol, isosorbide, isoidide, isomannide, hydrogenated bisphenol A, ethylene glycol, propylene glycol, polyethyleneglycol, diethylene glycol, neo pentyl glycol, 2,3 butanediol and sorbitol.

In a preferred embodiment, at least 50 weight % of the alcohol has a hydroxy functionality ≥3, more preferably ≥4.

Particularly preferred alcohols may be selected from: glycerol, pentaerythritol, 2,3-butanediol, mannitol, sorbitol, isoidide, isomannide, isosorbide, sorbitan and/or mixtures thereof. It is preferred that the polyol is from a biorenewable source.

Usefully alcohols may be present in the alkyd resin compositions in an amount of at least 10 wt-% and more preferably at least 20 wt-%, based on the total weight of compounds a, b, c and d. Conveniently the alcohol may be present in the alkyd resin compositions in an amount of less than 40 wt-% more conveniently less than 35 wt-%, even more conveniently less than 30 wt-%, especially more conveniently less than 28 wt-%, most conveniently less than 25 wt-%, for example less than 22 wt-%, based on the total weight of compounds a, b, c and d.

The alcohol may be present in the alkyd resin compositions in an amount of from 10 to 40 wt-%, preferably from 10 to 30 wt-%, more preferably from 15 to 25 wt-%, most preferably from 18 to 24 wt-%, for example 22 wt-% based on the total weight of compounds a, b, c and d.

Fatty Acid and Vegetable Oil (Compound c)

The alkyd resin composition further comprises fatty acids and/or vegetable oil.

It will be appreciated that there is a difference between a fatty acid and/or fatty acid derivative and a vegetable oil. Typically what is referred to herein as "oil" denotes a mixture of glycerol esters of one or more fatty acids. Thus for example linseed oil denotes a natural product, whereas linseed oil fatty acid denotes a mixture of fatty acids prepared from linseed oil.

A fatty acid is a carboxylic acid with a long aliphatic tail, which is either saturated or unsaturated. Most naturally occurring fatty acids have a chain of an even number of carbon atoms, from 4 to 28 (preferably from 8 to 28). Fatty acids are usually derived from triglycerides or phospholipids. As used herein, the term fatty acid denotes a linear hydrocarbon carboxylic acid that comprises at least one ethylenically unsaturated double bond and preferred fatty acids comprise at least two ethylenically unsaturated double bonds or more preferably comprise at least one linoleically unsaturated moiety. However saturated fatty acids may still be present in the alkyd resin compositions for other reasons. Preferred fatty acids are linear $C_{12-60}$ hydrocarbon mono carboxylic acids comprising at least one linoleically unsaturated moiety. As used herein the term 'fatty acid' also encompasses precursors for fatty acids, i.e. any component that under the conditions for alkyd resin preparation will transform and/or react to form a fatty acid.

For alkyd resins, unsaturated fatty acids or oils having an iodine number of at least 100 cg/g, preferably from 120 to 200 cg/g, are preferred where isolated and conjugated double bonds may be present. They are obtained, for example, from vegetable sources, such as soy oil, sunflower oil, linseed oil, safflower oil, and cottonseed oil or originate from tall oil distillation. Fatty acids having conjugated double bonds are obtained by catalytic isomerisation of natural fatty acids, from tung oil, calendula oil and/or from dehydrated castor oil. Conjugated oil is preferably obtained by Isomerisation of non-conjugated fatty acids and/or by dehydration of castor oil. The iodine number is defined according to DIN 53 241-1 as the quotient of that mass ml of iodine which is added on to the olefinic double bonds, with decolourisation, of a sample to be analysed and the mass of this sample (mass of the solid in the sample in the case of solutions or dispersions); its conventional unit is "g/(100 g)" or "cg/g". In addition, saturated oils or saturated fatty acids having 10 to 22 carbon atoms can be used in part or completely, as long as oxidative drying of the resin obtained is not impaired.

The alkyd resin composition may comprise vegetable oil. The use of a vegetable oil is advantageous with regard to high availability and low cost. Examples of vegetable oils are unsaturated oils such as soybean oil, tall oil, tung oil, calendula oil, rosin, sunflower oil, dehydrated castor oil and linseed oil.

The alkyd resin composition may comprise mixtures of fatty acids and vegetable oils; such mixtures may comprise two types of vegetable oil or fatty acid (for example soybean oil together with tung oil), mixtures comprising a fatty acid and a vegetable oil of the same type (for example tung oil together with tung oil fatty acid), and mixtures comprising a fatty acid and a vegetable oil of different types (for example tung oil together with soybean fatty acid). Preferably, the unsaturated oils and derived fatty acids are more folded unsaturated oils and derivates, i.e. oils or fatty acids having two, three or more double bonds. More preferred are tall oil, tung oil, calendula oil, rosin, sunflower oil, dehydrated castor oil, linseed oil, and corresponding fatty acids (for example tung oil fatty acid or soybean fatty acid). The most preferred are soybean fatty acid and/or tung oil, more preferred substantially tung oil. By substantially tung oil is here meant that only smaller amounts of other compounds are present.

In one embodiment the fatty acid and/or the vegetable oil has at least one eleostearic moiety. Herein by eleostearic moiety it is meant a moiety that consists of 3 conjugated double bonds. Examples of fatty acids or vegetable oils containing such moieties include among others eleostearic acid, tung oil or calendula oil. These have in their structure one or more eleostearic moeities. The advantage of using a fatty acid and/or vegetable oil containing an eleostrearic moiety is that the alkyd resin has a much better air-drying performance than using a non-eleostearic moiety containing fatty acid and/or vegetable oil. Tung oil is composed primarily of eleostearic acid which is an 18 carbon fatty acid having three conjugated double bonds (an eleostearic moiety).

Usefully fatty acids and/or vegetable oils may be present in the alkyd resin compositions in an amount of at least 30 wt-%, preferably of at least 35 wt-%, more preferably at least 40 wt-% and most preferably at least 50 wt-%, based on the total weight of compounds a, b, c and d. Conveniently the fatty acids or vegetable oils may be present in the alkyd resin compositions in an amount of less than 70 wt-%, more conveniently less than 65 wt-%, even more conveniently less than 60 wt-%, especially more conveniently less than 58 wt-%, most conveniently less than 55 wt-%, based on the total weight of compounds a, b, c and d.

The fatty acids or vegetable oils may be present in the alkyd resin compositions in an amount of from 30 to 70 wt-%, preferably from 40 to 60 wt-%, more preferably from 45 to 55 wt-%, for example 47 wt-% based on the total weight of compounds a, b, c and d.

Mono or Polyfunctional Compound (Compound d)

The alkyd resin composition can optionally comprise an either biobased or non-biobased mono and/or polyfunctional compound capable of esterification, which compound is different from the compounds according to anyone of formulas Ia-e, the alcohol or the fatty acids or vegetable oils. Examples of mono and polyfunctional compounds capable of esterification are mono and polyfunctional compounds containing OH, COOH and/or NCO groups. Examples of such compounds containing OH and/or COOH groups are: Succinic acid lysine diimide or lysine disuccinimide (made from 1 mole of lysine and 2 moles of succinic acid or succinic anhydride), phenyl alanine succinimide (made from 1 mole of phenyl alanine and 1 mole of succinic acid or succinic anhydride), glycine succinimide (made from 1 mole of glycine and 1 mole of succinic acid or succinic anhydride), benzoic acid, succinic acid or succinic anhydride, adipic acid, sebacic acid, azelaic acid, terephthalic acid, phthalic acid, phthalic anhydride, trimellitic anhydride, citric acid, citric anhydride, citraconic acid, citraconic anhydride, isophthalic acid, itaconic acid, itaconic anhydride, tetrahydrophthalic acid, tetrahydrophthalic anhydride, hexahydrophthalic acid, hexahydrophthalic anhydride, monomethyl tetrahydrophthalic acid, monomethyl tetrahydrophthalic anhydride, monomethyl hexahydrophthalic acid, monomethyl hexahydrophthalic anhydride and/or any suitable mixtures thereof. Instead of the (di)carboxylic acids the corresponding alkyl esters may also be used. Examples of such compounds containing NCO groups are polyfunctional isocyanate compounds, preferably diisocyanates are used. Examples of polyfunctional isocyanate compounds are ethylene diisocyanate, 1,6-hexamethylene diisocyanate, isophorone diisocyanate, cyclohexane-1, 4-diisocyanate, 4,4'-dicyclohexylmethane diisocyanate, p-xylylene diisocyanate, α,α'-tetramethylxylene diisocyanate, 1,4-phenylene diisocyanate, 2,4-toluene diisocyanate, 2,6-toluene diisocyanate, 4,4'-diphenylmethane diisocyanate, polymethylene polyphenyl polyisocyanates, 2,4'-diphenylmethane diisocyanate, 3(4)-isocyanatomethyl-1-methyl cyclohexyl isocyanate, 1,5-naphthylene diisocyanate, Desmodur HDTLV and mixtures thereof. Preferred polyisocyanates are isophorone diisocyanate, 4,4'-dicyclohexylmethane diisocyanate, toluene-diisocyanate and 4,4'-diphenylmethane diisocyanate.

In an embodiment the mono and/or polyfunctional compound is present in such an amount such that the amounts of the compounds according to anyone of formulas Ia-e, the alcohol, the fatty acids, the vegetable oils and the mono and polyfunctional compound total 100 wt % and the amounts for each component in the alkyd resin composition also satisfy the preferred or more preferred amounts given for each component herein. The presence of the mono and polyfunctional compound is optional as in a yet further embodiment the mono and polyfunctional compound may also be absent (0% by weight) in the alkyd resin composition and for example the alkyd resin composition may then consist of the compounds according to anyone of formulas Ia-e, the alcohol, the fatty acids and/or vegetable oils.

Components or parts of components that do not fall within the definitions of the compounds according to anyone of formulas Ia-e, the alcohol, the fatty acids and/or vegetable oils and which components are capable of esterification are considered to form part of the optional mono or polyfunctional compound.

The amounts by weight for the compounds according to anyone of formulas Ia-e, the alcohol, the fatty acids and/or vegetable oils and the mono and/or polyfunctional compound given above are calculated based on the total being 100 wt %. If desired an esterification or trans-esterification catalyst can be used for the synthesis of the alkyd resin. Such catalysts are added on top of the total of the compounds according to anyone of formulas Ia-e, the alcohol, the fatty acids and/or vegetable oils and the mono and/or polyfunctional compound. Examples of such catalysts are tetrabutyl titanate, zinc acetate, Sn-compounds, like Sn-salts, monoalkyl Sn complexes etc.

There is an increasing demand to use bio renewable monomers in order to improve the sustainability of the resins used in for example coating applications. In view of concerns about depletion of fossil fuel resources or an increase in carbon dioxide in the air that poses a global scale environmental problem in recent years, methods for producing raw materials of these polymers from biomass resources have attracted a lot of attention. Since these resources are renewable and therefore have a carbon neutral biomass, such methods are expected to gain in particular importance in the future. It is therefore a preferred feature of the present invention and the aspects described herein that where possible the components used herein as far as possible are biorenewable.

Preferably at least 20 wt-%, more preferably at least 30 wt-%, and especially 40 wt-% of the components used to form the alkyd resin are derived from at least one biorenewable material. Biorenewable materials may be obtained fully or in part from biorenewable sources. Thus it is preferred to also measure the carbon-14 content to determine the biorenewability content of the components of the alkyd resin. The term bio-based is also used herein as a synonym for biorenewable (as defined herein).

The content of carbon-14 ($^{14}C$) is indicative of the age of a bio based material. It is known in the art that $^{14}C$, which has a half-life of about 5,700 years, is found in bio renewable materials but not in fossil fuels. Thus, "biorenewable materials" or "biomass" refer to organic materials in which the carbon comes from non-fossil biological sources. Examples of biorenewable materials include, but are not limited to, sugars, starches, corns, natural fibres, sugarcanes, beets, citrus fruits, woody plants, cellulosics, lignocelluosics, hemicelluloses, potatoes, plant oils, other polysaccharides such as pectin, chitin, levan, and pullulan, and a combination thereof. $^{14}C$ levels can be determined by measuring its decay process (disintegrations per minute per gram carbon or dpm/gC) through liquid scintillation counting. In one embodiment of the present invention, the alcohol component of the alkyd resin comprises at least about 1.5 dpm/gC (disintegrations per minute per gram carbon) of carbon-14, more preferably at least 2 dpm/gC, most preferably at least 2.5 dpm/gC, and especially at least 4 dpm/gC.

The invention also relates to an alkyd resin obtained by polycondensation of the compounds of the alkyd resin composition as defined above.

Therefore there is provided an alkyd resin (preferably having low VOC) obtained by reaction in a process (I) between the compounds according to anyone of formulas Ia-e, the alcohol, the fatty acids and/or vegetable oils and, optionally, the mono and/or polyfunctional compound to obtain an alkyd resin composition. VOC denotes volatile organic compounds which are organic compounds that have a boiling point from 50 to 250° C. under 1 atmosphere pressure. Low VOC denotes that the amount of VOC present is less than 100 g/l, if a liquid material and less than 100 g per kg if a solid material.

Another aspect of the present invention provides a process comprising a further optional blending step (II) performed after polycondensation process step (I) where step (II) comprises
   (II) adding a diluent to the alkyd resin obtained from step (I) to form an admixture therewith; wherein the diluent comprises an ethylenically unsaturated $C_{5-6}$ hydrocarbon dicarboxylic acid (preferably $C_5$ diacid), ester thereof and/or anhydride thereof, being reactive as a dienophile and/or enophile with the alcohol and/or the fatty acids and/or vegetable oils and/or (where present) the optional mono and/or polyfunctional compound;
wherein optional diluent is present in an amount of from 1 to 30 parts by weight with respect to 100 parts of the compounds according to anyone of formulas Ia-e, the alcohol, the fatty acids and/or vegetable oils and, optionally, the mono and/or polyfunctional compound from step (I).

The diluent may also be used as an additional reactant in process step (I) and/or as a diluent in the blending step (II). Examples of reactive diluents are dimethylitaconate, dibutylitaconate, α-methylene-γ-butyrolactone.

The invention also relates to a coating obtainable by applying a layer of the alkyd resin composition as defined above or a layer of the alkyd resin, obtained after polycondensation of the alkyd resin composition, on an object followed by curing of the layer.

The curing may be by any suitable means, such as thermally, by radiation, by oxidation (with oxygen from the atmosphere) and/or by use of a cross-linker.

Examples of coating compositions which can be used for obtaining a coating are aqueous coating compositions and solvent-borne coating compositions.

Optionally aqueous coating compositions may also comprise a co-solvent. A co-solvent, as is well known in the coating art, is an organic solvent employed in an aqueous composition to ameliorate the drying characteristics thereof, and in particular to lower its minimum film forming temperature. The co-solvent may be solvent incorporated or used during preparation of polymers or may have been added during formulation of the aqueous composition.

The coating composition is particularly useful as or for providing the principle component of coating formulations (i.e. composition intended for application to a substrate without further treatment or additions thereto) such as protective or decorative coating compositions (for example paint, lacquer or varnish) wherein an initially prepared composition optionally may be further diluted with water and/or organic solvents, and/or combined with further ingredients or may be in more concentrated form by optional evaporation of water and/or organic components of the liquid medium of an initially prepared composition.

The coating may be applied to a variety of substrates including wood, board, metals, stone, concrete, glass, cloth, leather, paper, plastics, foam and the like, by any conventional method including brushing, dipping, flow coating, spraying, and the like. The coating may also be used to coat the interior and/or exterior surfaces of three-dimensional articles. The carrier medium may be removed by natural drying or accelerated drying (by applying heat) to form a coating.

The alkyd resin coating composition may contain other conventional ingredients including pigments, dyes, emulsifiers, surfactants, plasticisers, thickeners, heat stabilisers, levelling agents, anti-cratering agents, fillers, sedimentation inhibitors, UV absorbers, antioxidants, dispersants, reactive diluents, waxes, neutralising agents, adhesion promoters, defoamers, co-solvents, wetting agents and the like introduced at any stage of the production process or subsequently. It is possible to include fire retardants (such as antimony oxide) to enhance the fire retardant properties.

The invention is further directed to the use of the compounds of formulas Ia, Ib, Ic, Id or Ie to make a polymer or resin composition.

The invention is also directed to an object containing coating layers obtainable by the application of the alkyd resin composition described above followed by curing.

The present invention further relates to an alkyd emulsion comprising an alkyd resin as described above, which emulsion is water borne, and where optionally at least one surfactant (preferably a mixture of nonionic and ionic surfactants) is added after the reaction of Components a, b, c and d and/or where optionally at least one surfactant (preferably a mixture of nonionic and ionic surfactants) is added during the reaction of components a to d. The present invention further also relates to an alkyd resin as described above which is solvent borne or a solid.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention will now be described in detail with reference to the following non limiting examples which are by way of illustration only.

EXAMPLES

Unless otherwise indicated all the tests herein are carried out under standard conditions as also defined herein.

Acid Number

The acid number (or AN) is given as the mass of potassium hydroxide (KOH) in milligrams that is required to neutralize one gram of the tested substance and is used as a measure of the concentration of carboxylic acid groups present. AN is determined conventionally by titration and/or using ASTM D974.

Gloss Measurement Method:

Gloss measurements were carried out on a BYK Gardner micro TRI gloss 20 60 85 glossmeter in accordance with ASTM D523 89.

KÖNIG HARDNESS

König hardness was determined following DIN 53157 NEN 5319 using an Erichsen hardness equipment. The values are given in seconds (s). Preferably the unpigmented composition of the invention has a König hardness of at least 30 seconds after 4 weeks.

Molecular Weight Determination by GPC (Weight Average Mw):

Unless the context dictates otherwise, the molecular weights referred to in this application are weight average molecular weight (also denoted herein as Mw) as determined on an Alliance Waters 2695 GPC with two consecutive PL-gel columns, type Mixed-C, 1/d=300/7.5 mm (Polymer Laboratories), size of column particles 10 μm, using stabilised tetrahydrofuran (THF) modified with 0.8% acetic acid as the eluent at 1 mL/min at 40° C. and using an Alliance Waters 2414 refractive index detector at 40° C. A set of polystyrene standards with a molecular weight range of from 500 to $7 \times 10^6$ g/mol was used to calibrate the GPC equipment.

Molecular Weight Determination by GPC (number average Mn):

Unless the context dictates otherwise where a number average molecular weight (also denoted herein as Mn) is mentioned this is measured using the same apparatus in the manner described above. The dispersity was determined by dividing Mw by Mn.

Particle Size

The particle size values given herein may be measured using a chromatographic technique in a Polymer Labs Particle Size Distribution Analyser (PSDA) and the values used herein are the volume mean. The particle sizes are quoted as a linear dimension which would be the diameter of an approximate spherical particle having the same volume as the volume mean measured.

Standard Conditions

As used herein, unless the context indicates otherwise, standard conditions (e.g. for drying a film) means a relative humidity of 50%±5%, ambient temperature (23° C.±2°) and an air flow of less than or equal to 0.1 m/s.

Drying Properties (Cotton Wool Dust Free Time (DFT) and Tack Free Time (TFT) Tests).

A cotton wool adhesion test measures the rate of surface drying of a coating film. The cotton wool adhesion test was conducted on a coating film applied with a 100 μm slit applicator on a glass plate. After applying the coating composition, a swatch of cotton wool (a loose ball of approximately 0.2 g and a diameter of approximately 3 cm) was dropped from a height of 5 cm on the paint film. After 10 seconds the glass panel was turned over 180° and it was observed if the cotton wool dropped off without leaving cotton fibres on the surface. When the cotton wool did not stick to the surface, the time was recorded as the dust free time. For the tack free time the same procedure was used, but now a weight of 1 kg was placed on the cotton wool. The tack free time was always determined after dust-free properties were reached.

Water Resistance:

A 100 μm wet film was cast on a Leneta chart and dried for 24 hours under standard conditions. Then three drops of water were placed on the film and one drop of water was removed after 30 minutes, a further one after one hour and the final one after 3 hours. The water resistance was assessed immediately after removal of the water and after 24 hours. The rating for water resistance is from 0=very poor, dissolved, 3=acceptable, 5=excellent, no damage of the coating.

Water resistance can also be measured quantitatively using the following test. The composition to be tested is applied to a film as described above in the wet adhesion test. The coated test specimens were soaked in tap water at 40 degrees C. for seven days at room temperature (20 degree C.). The weight gain was recorded at end of this period (and at suitable intervals throughout) to calculate the relative water uptake of the specimens. Other methods may also be used to evaluate the water resistance of compositions of the invention, such as the method described below.

Early water resistance may be measured in as follows. A 250 μm thick layer of the polymer coating to be tested is applied to a Leneta chart. The polymer is allowed to dry for 24 hours at room temperature to form a film coating. Three drops of water are applied to the film. The first drop is removed after 15 minutes, the second drop after 30 minutes and the third drop after 120 minutes. A film with excellent water resistance will not turn white nor will it blister, this rated "5". Poor water resistance, where the film either strongly whitens or blisters, is rated "0".

Yellowing:

Colour change due to yellowing is measured according to CieLab. A coating film is applied with a 100 μm slit applicator on a glass plate and dried for one week at room temperature. Then initial colour according to CieLab (L-value, a-value, b-value) is measured and b-value recorded. Next the film is stored in an oven at 50° C. for one week. Again colour is measured and change in b-value is recorded as Δb. The higher Δb, the stronger the yellowing is. Reliability is improved by further measurements after 2 weeks. Reduced Yellowing is defined herein and preferred polyester resins and compositions of the invention exhibit Reduced Yellowing.

The applicant has surprisingly found that unlikely prior art imide resins in general the imide based resins of the invention are not strongly coloured and also they do not yellow to a great extent.

Preparation Example DMTHPA

The adduct of isoprene and citraconic anhydride was prepared by mixing the monomers (isoprene in 5% excess) with 250 ppm hydroquinone in a stirred pressure reactor and heating to 85° C. for 12 hours. After a distillation step about 92% product was isolated as a mobile liquid and identified as a mixture of 2 isomers of dimethyl tetrahydrophthalic anhydride (DMTHPA) by H NMR. Purity was estimated 99.8% by GC.

Preparation Example DMHHPA

DMTHPA was hydrogenated using a supported palladium catalyst in a stirred pressure reactor. H NMR showed conversion of the C=C double bond, GC showed presence of 4 compounds being formed and mass spectrometry (using chemical ionization) showed that the MW of all 4 peaks is 182 (MW of Diels-Alder adduct starting material is 180). Further fragmentation pattern of all 4 peaks (using electron impact) indicated they are all isomers/diastereomers of dimethyl hexahydrophthalic anhydride (DMHHPA).

Example 1: Imide

DMTHPA glycine imide was prepared by introducing in a 1 liter glass reactor, fitted with mechanical stirrer, nitrogen inlet, thermocouple and Dean-Stark trap, 180.2 grams (1 mole) DMTHPA prepared as described above, 75.1 grams (1 mole) glycine and 100 grams of xylene; heating the mixture to reflux at 150° C. for about 4 hours when 17.2 grams of water was collected in the trap. The brown liquid material was poured and out solids content was determined to be 63.3%. Acid value was determined to be 248 mgKOH/g on solid. GPC showed a dispersity of 1.06. Purity was estimated to be at least 96%, based on water distillate and acid value.

Example 2: Imide

DMHHPA glycine imide was prepared by introducing in a 1 liter glass reactor, fitted with mechanical stirrer, nitrogen inlet, thermocouple and Dean-Stark trap, 182.2 grams (1 mole) DMHHPA prepared as described above, 75.1 grams (1 mole) glycine and 100 grams of xylene; heating the mixture to reflux at 150° C. for about 4 hours when 17.2 grams of water was collected in the trap. The brown liquid material was poured out and solids content was determined to be 61.4%. Acid value was determined to be 261 mgKOH/g on solid. GPC showed a dispersity of 1.08. Purity was estimated to be at least 90%, based on water distillate and acid value.

Example 3: Imide

MHHPA phenylalanine imide was prepared by introducing in a 1 liter glass reactor, fitted with mechanical stirrer, nitrogen inlet, thermocouple and Dean-Stark trap, 117.7 grams (0.7 mole) methyl hexahydrophthalic anhydride (MHHPA), 115.5 grams (0.7 mole) phenylalanine and 150 grams of xylene; heating the mixture to reflux at 150° C. for about 4 hours when 12.3 grams of water was collected in the trap. The brown liquid material was poured out and solids content was determined to be 62.7%. Acid value was determined to be 181 mgKOH/g on solid. GPC showed a dispersity of 1.06. Purity was estimated to be at least 98%, based on water distillate and acid value.

Example 4: Imide

DMHHPA lysine diimide was prepared by introducing in a 1 liter glass reactor, fitted with mechanical stirrer, nitrogen inlet, thermocouple and Dean-Stark trap, 182.2 grams (1 mole) DMHHPA prepared as described above, 73.1 grams (0.5 mole) lysine and 110 grams of xylene; heating the mixture to reflux at 150° C. for about 4 hours when 19.0 grams of water was collected in the trap. The brown liquid material was poured out and solids content was determined to be 64.0%. Acid value was determined to be 139 mgKOH/g on solid. GPC showed a dispersity of 1.07. Purity was estimated to be at least 91%, based on water distillate and acid value.

Example 5: Resin

An alkyd based on DMHHPA glycine imide was prepared by reacting in a 2 liter glass reactor, fitted with mechanical stirrer, nitrogen inlet, thermocouple and Dean-Stark trap, 384 grams of soybean oil fatty acids, 224 grams of pentaerythritol, 222 grams of Imide from example 2, and 240 grams of phthalic anhydride using azeotropic water removal at 235° C. After reaching an acid value below 10 mgKOH/g, the reaction was stopped. After cooling down 400 grams of xylene were added to obtain a clear low viscosity liquid resin with properties as shown in table 1.

Example 6: Resin

An alkyd based on MHHPA phenylalanine imide was prepared by reacting in a 1 liter glass reactor, fitted with mechanical stirrer, nitrogen inlet, thermocouple and Dean-Stark trap, 228 grams of soybean oil fatty acids, 133 grams of pentaerythritol, 136 grams of Imide from example 3, and 143 grams of phthalic anhydride using azeotropic water removal at 235° C. After reaching an acid value below 10 mgKOH/g, the reaction was stopped. After cooling down 200 grams of xylene were added to obtain a clear low viscosity liquid resin with properties as shown in table 1.

Example 7: Resin

An alkyd based on DMHHPA lysine diimide was prepared by reacting in a 2 liter glass reactor, fitted with mechanical stirrer, nitrogen inlet, thermocouple and Dean-Stark trap, 382 grams of soybean oil fatty acids, 222 grams of pentaerythritol, 219 grams of Imide from example 4, and 239 grams of phthalic anhydride using azeotropic water removal at 235° C. After reaching an acid value below 10 mgKOH/g, the reaction was stopped. After cooling down 400 grams of xylene were added to obtain a clear low viscosity liquid resin with properties as shown in table 1.

Comparative Example A: Resin

A comparative resin was prepared by reacting in a 2 liter glass reactor, fitted with mechanical stirrer, nitrogen inlet, thermocouple and Dean-Stark trap, 382 grams of soybean oil fatty acids, 260 grams of pentaerythritol, 160 grams of benzoic acid, 280 grams of phthalic anhydride and a suitable amount of xylene using azeotropic water removal at 235° C. until an acid value below 12 mgKOH/g was obtained. After cooling down further xylene was added to obtain a clear low viscosity liquid resin with properties as shown in table 1.

TABLE 1

Resin characteristics

| Example | Resin based on: | Imide example | Solids content % | Acid value mgKOH/g | Mn Da | Mw kDa |
|---|---|---|---|---|---|---|
| 5 | DMHHPA glycine imide | 2 | 68.3 | 8.8 | 2750 | 10 |
| 6 | MHHPA phenylalanine imide | 3 | 72.8 | 9.1 | 2500 | 12 |
| 7 | DMHHPA lysine diimide | 4 | 70.3 | 9.1 | 2740 | 12 |
| Comp A | Benzoic acid | none | 70.4 | 11.1 | 2600 | 22 |

Example 8: Paints

Paints were produced by mixing in a Cowless dissolver resin solution (44 grams solid resin), 28 grams of Tioxide TR 92 (pigment) and 0.30 grams of Nuosperse FA 601 (dispersant) and milling them into a mill paste. To this paste were added under stirring 0.31 grams Borchers OxyCoat (Fe drier) and xylene to give application viscosity. These paints showed the following properties (table 2).

TABLE 2

Paint properties

| Resin from example: | Comp A | 5 | 6 | 7 |
|---|---|---|---|---|
| Drying dust free time (hrs:min) | 0:20 | 0:20 | 1:00 | 0:20 |
| Drying tack free time (hrs:min) | 2:30 | 2:30 | 3:30 | 3:20 |
| König Hardness 1 day | 30 | 38 | 48 | 34 |
| König Hardness 7 days | 77 | 86 | 98 | 83 |
| Yellowing in the dark at 50° C. | | | | |
| b* Initial | 1.96 | 2.35 | 2.03 | 2.12 |
| Δb* after 7 days 50° C. | 0.93 | 0.75 | 0.84 | 0.83 |
| Δb* after 14 days 50° C. | 1.12 | 1.08 | 1.17 | 1.18 |
| Gloss, after 2 weeks, 20° | 86 | 85 | 88 | 87 |
| Gloss, after 2 weeks, 60° | 94 | 93 | 94 | 93 |

The results show that the paints (Examples 5, 6 and 7) formulated with resins containing imides of the invention show better hardness results in comparison with prior art Comp A, whereas yellowing and gloss retention results of the resins of the invention and the comparative experiment are virtually the same. Moreover, examples 6 and 7 have a significantly higher biobased content compared to comparative experiment A.

The invention claimed is:

1. An alkyd resin composition comprising
   a. 1-60 wt % of an imide compound according to anyone of formulas Ia, Ib, Ic, Id or

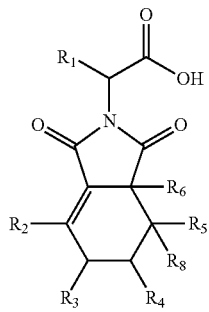

Ia

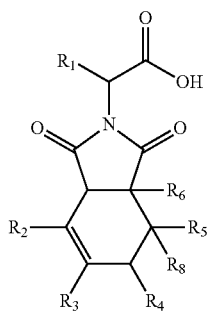

Ib

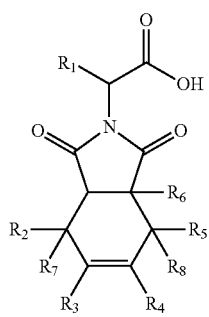

Ic

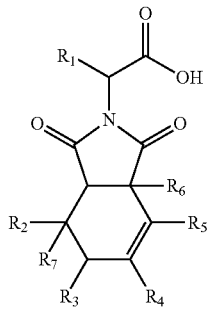

Id

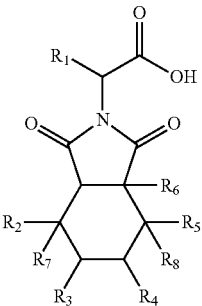

Ie wherein R1 is H or a C1-C20 optionally substituted hydrocarbon group;
R2 and R5 are independently H, or a C1-C20 hydrocarbon group;
R3 and R4 are independently H, or a C1-C20 hydrocarbon group;
R6 is H or a methyl group;
R7 and R8 are independently H, methyl or ethyl;
   b. 10-40 wt % of an alcohol having a number average hydroxy functionality ≥2.0;
   c. 30-70 wt % of fatty acids or vegetable oils;
   wherein the wt % is determined relative to the total of weight of compounds a, b, and c.

2. The alkyd resin composition according to claim 1, wherein R6 is methyl.

3. The alkyd resin composition according to claim 1, wherein R1 is selected from H, methyl, hydroxymethyl, 1-hydroxyethyl, isopropyl, sec-butyl, 2-methyl-propyl, 2(methylthio)ethyl, benzyl, tolyl and parahydroxytolyl.

4. The alkyd resin composition according to claim 1, wherein R1 is selected from H and benzyl.

5. The alkyd resin composition according to claim 1, wherein R2 is H, methyl or ethyl.

6. The alkyd resin composition according to claim 1, wherein R5 is H, methyl or ethyl.

7. The alkyd resin composition according to claim 1, wherein R2 and R5 are independently H or methyl.

8. The alkyd resin composition according to claim 1, wherein R3 is H.

9. The alkyd resin composition according to claim 1, wherein R4 is H.

10. The alkyd resin composition according to claim 1, wherein R7 and R8 are both H.

11. An alkyd resin obtained by polycondensation of the alkyd resin composition according to claim 1.

12. A coating obtained by applying a layer of an alkyd resin according to claim 11 on an object, followed by curing of the layer.

13. An object containing coating layers obtained by the application of an alkyd resin according to claim 11, followed by curing.

14. An alkyd emulsion comprising an alkyd resin according to claim 11, wherein the alkyd emulsion is water borne.

* * * * *